United States Patent [19]

Antons

[11] Patent Number: 5,731,479
[45] Date of Patent: *Mar. 24, 1998

[54] PROCESS FOR THE PREPARATION OF OPTICALLY ACTIVE ALCOHOLS

[75] Inventor: Stefan Antons, Leverkusen, Germany

[73] Assignee: Bayer Aktiengesellschaft, Leverkusen, Germany

[*] Notice: The term of this patent shall not extend beyond the expiration date of Pat. No. 5,536,879.

[21] Appl. No.: 567,787

[22] Filed: Dec. 5, 1995

[30] Foreign Application Priority Data

Dec. 12, 1994 [DE] Germany ............... 44 44 109.6

[51] Int. Cl.$^6$ .................................. C07C 27/00
[52] U.S. Cl. ................. 568/864; 568/853; 568/841; 568/811; 568/814; 568/812
[58] Field of Search .................. 568/864, 853, 568/841, 811, 814; 566/812

[56] References Cited

U.S. PATENT DOCUMENTS

| | | |
|---|---|---|
| 2,607,805 | 8/1952 | Gresham . |
| 2,607,807 | 8/1952 | Ford . |
| 4,273,947 | 6/1981 | Novotny . |
| 5,536,879 | 7/1996 | Antons et al. ............... 564/503 |

FOREIGN PATENT DOCUMENTS

| | | |
|---|---|---|
| 3802981 | 8/1989 | Germany . |
| 9319030 | 9/1993 | WIPO . |

OTHER PUBLICATIONS

J.E. Carnahan, et al., J.A.C.S., vol. 77, pp. 3766–3768, (1955).

H. Seki, et al., Chem. Pharm. Bull., vol. 13, No. 8, pp. 995–1000, (1965).

M.J. Mckennon, et al., J. Org. Chem., vol. 58, No. 13, pp. 3568–3571, (1993).

A. Abiko, et al., Tetrahedron Letters, vol. 33, No. 38, pp. 5517–5518, (1992).

A. Giannis, et al., Angew. Chem. Int. Ed. Engl., vol. 28, No. 2, pp. 218–220, (1989).

H.C. Brown, et al., J.A.C.S., vol. 78, pp. 2582–2588, (1956).

O. Vogl, et al, Monatshefte der Chemie, vol. 13, pp. 541–544, 1952.

P Karrer, et al, Helv. Chem. Acta., vol. 13, pp. 1617–1623, 1948.

E. Muller, et al, Methoden der Organischen Chemie, (Houben–weyl), vol. V1/1b, pp. 103–107, 4th ed., Georg Thieme Verlag, New York, 1984.

*Primary Examiner*—Samuel Barts
*Attorney, Agent, or Firm*—Sprung Kramer Schaefer & Briscoe

[57] ABSTRACT

Optically active alcohols are prepared by reducing optically active carboxylic acids with hydrogen in the presence of ruthenium catalysts.

14 Claims, No Drawings

PROCESS FOR THE PREPARATION OF OPTICALLY ACTIVE ALCOHOLS

The present invention relates to a process for the preparation of optically active alcohols by reduction of the corresponding optically active carboxylic acids.

It is known that optically pure alcohols can be prepared from optically pure carboxylic acids on the laboratory scale by reduction with lithium aluminum hydride or activated sodium borohydride (see Monatshefte der Chemie 83, 541 (1952), Helv. Chim. Acta 31, 1617 (1949), Chem. Pharm. Bull. 13, 995 (1965.), JAGS 78, 2582 (1956), JOC 58, 3568 (1993), Angew. Chem. Int. Ed. 28, 218 (1989), Tetrahedron Letters 33, 5517 (1992) and German Offenlegungsschrift 3 827 789). The required reducing agents are not suitable for use on the industrial scale because they are particularly difficult to handle and are very cost-intensive.

It is also known that carboxylic acids can be catalytically reduced to alcohols with hydrogen. A summary of this subject can be found in Houben-Weyl, Methoden der organischen Chemie (Methods of Organic Chemistry), 4th edition, vol. VI/1b, pages 103–107 (1984). Nothing has been disclosed about the stereoselectivity of this reduction when using optically active carboxylic acids. If ruthenium-containing catalysts are used (loc. cit. p. 106), the reduction demands relatively high temperatures and very high pressures, e.g. temperatures of 145° to 190° C. and pressures of 700 to 950 bar. Such processes are not suitable for the preparation of optically active alcohols because racemizations and degradation reactions take place under the drastic reaction conditions which have to be applied.

There is therefore still a need for a good, simple and inexpensive process for the preparation of optically active alcohols.

A process for the preparation of optically active alcohols has now been found which is characterized in that optically active carboxylic acids are reduced with hydrogen at temperatures below 160° C. and pressures below 250 bar, in the presence of ruthenium catalysts.

Examples of optically active carboxylic acids which can be used in the process according to the invention are those of the formula (I):

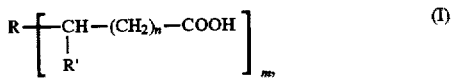

in which
m is 1, 2 or 3,
n is zero or an integer from 1 to 5 and
R' is a monovalent radical selected from the group comprising linear and branched $C_1$–$C_{12}$-alkyl, $C_7$–$C_{12}$-aralkyl, $C_6$–$C_{10}$-aryl and $C_1$–$C_{12}$-alkoxy radicals or is hydroxyl or halogen, and
if m=1
R is a monovalent radical selected from the group comprising linear and branched $C_1$–$C_{12}$-alkyl, $C_7$–$C_{12}$-aralkyl, $C_6$–$C_{10}$-aryl and $C_1$–$C_{12}$-alkoxy radicals or is a halogen or hydroxyl radical which is different from R',
if m=2
R is absent or is a divalent radical selected from the group comprising linear and branched $C_1$–$C_{12}$-alkyl and $C_7$–$C_{12}$-aralkyl radicals, and
if m=3
R is a trivalent radical selected from the group comprising linear and branched $C_1$–$C_{12}$-alkyl and $C_7$–$C_{12}$-aralkyl radicals, giving optically active alcohols of the formula (II):

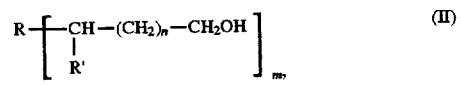

in which
m, n, R' and R are as defined for the formula (I).
Preferably, in the formulae (I) and (II),
m is 1 or 2,
n is zero, 1 or 2 and
R' is linear or branched $C_1$–$C_4$-alkyl, benzyl, hydroxyl, fluorine, chlorine or bromine, and
R is different from R' and is linear or branched $C_1$–$C_4$-alkyl, benzyl, hydroxyl, fluorine or chlorine.

A further preference is for one of the radicals R' and R to be hydroxyl.

If m is 2 or 3, i.e. there are 2 or 3 molecular moieties CH(R')—(CH$_2$)n—COOH present in the starting material, these molecular moieties can be identical or different in respect of the definitions of n and R'.

If R' and R are alkyl, aralkyl, aryl and/or alkoxy radicals, these can optionally be substituted, e.g. by halogen, hydroxyl, $C_1$–$C_4$-alkoxy, thiol, amino and/or $C_1$–$C_4$-alkylamino radicals. R' and/or R preferably contain fewer than four such substituents. Reductions and/or cleavage reactions may also take place at such substituents.

If R' and R are alkyl, aralkyl, aryl or alkoxy radicals, these can optionally contain heteroatoms, e.g. oxygen, sulphur and/or nitrogen atoms, in the alkyl chain and/or in the aryl moiety. Preferably, fewer than 3 such heteroatoms are present.

If R' and R are aralkyl or aryl radicals, these can also be partially or fully hydrogenated.

Particularly preferably, the acid used in the process according to the invention is optically active lactic acid, optically active tartaric acid, optically active 2-chloropropionic acid or optically active malic acid, giving optically active propane-1,2-diol, optically active 1,2,3,4-tetrahydroxybutane, optically active 2-chloropropanol or optically active 1,2,4-trihydroxybutane respectively.

Suitable ruthenium catalysts are elemental ruthenium and ruthenium compounds, both of which can be used as such or applied to a support. Examples of catalysts are finely divided elemental ruthenium, ruthenium oxides, ruthenium hydroxides and ruthenium halides. Examples of suitable supports are carbon, aluminium oxides, silicon dioxides, silicates, alkaline earth metal carbonates and alkaline earth metal sulphates. Supported catalysts can contain for example 1 to 20% by weight of elemental ruthenium or the corresponding amount of ruthenium compounds.

Based on 1 mol of optically active carboxylic acid starting material, it is possible to use e.g. 0.1 to 10 g of elemental ruthenium or ruthenium compounds or 1 to 50 g of ruthenium-containing supported catalyst.

The reduction according to the invention is preferably carried out in the presence of a solvent for the optically active carboxylic acid and the optically active alcohol. Examples of suitable solvents are water, water-miscible organic solvents and mixtures of the two. Water-miscible solvents which may be mentioned are lower alcohols and water imiscible ethers. Preferred solvents are water and mixtures containing water and lower alcohols or tetrahydrofuran.

Suitable reaction conditions for the process according to the invention are e.g. temperatures in the range 50° to 150° C. and pressures in the range 5 to 250 bar. The process is preferably carried out at 70° to 130° C. and 50 to 220 bar.

To work up the reaction mixture, it is possible for example firstly to cool it and separate off the catalyst, e.g. by filtration, and then to distil off the readily volatile constituents present, if necessary under slightly reduced pressure, and fractionate the residue under vacuum. The catalyst which has been separated off can be reused, as can the solvent.

The process according to the invention can be carried out continuously or batchwise.

The surprising advantages of the process according to the invention are that it provides access to optically active alcohols in a simple manner, at relatively low temperatures and pressures, at low cost and with a high selectivity (enantiomeric excess, ee, usually over 90%).

EXAMPLES

Example 1

4 g of Ru black and 89 g of L-(+)-lactic acid were placed in 700 g of water in a 1.3 l stainless steel autoclave. After flushing with nitrogen, the apparatus was closed and brought to a hydrogen pressure of 100 bar. Over 2 hours the temperature was raised to 80° C. and the hydrogen pressure to 200 bar. The mixture was stirred at 80° C. and 200 bar until the uptake of hydrogen had ended, it was then cooled to room temperature, the catalyst was filtered off and the water was distilled off. The residue obtained was distilled under nitrogen at 16 mbar to give 64 g of L-(+)-propane-1, 2-diol (b.p. 74° C.; $[\alpha]_D^{20}$ +16.2°; ee>97%).

Examples 2 to 7

The procedure was as in Example 1 except that other catalysts were used. The details are given in Table 1.

TABLE 1

| | Catalyst | | Propane-1,2-diol obtained | |
|---|---|---|---|---|
| Ex. no. | Type | Amount (g) | Yield (% of theory) | ee for L form (%) |
| 2 | 10% by weight Ru-on-carbon | 20 | 74 | >97 |
| 2 | RuO$_2$ reduced at 150° C. | 2 | 88 | >97 |
| 4 | 5% by weight Ru-on-Al$_2$O$_3$ | 20 | 68 | >97 |
| 5 | RuO$_2$ reduced at 150° C. | 10 | 86 | >97 |
| 6 | 5% by weight Ru-on-carbon | 10 | 35 | 97 |
| 7 | 5% by weight Ru-on-carbon | 20 | 64 | >97 |

Examples 8 to 10

The procedure was as in Example 1 except that higher temperatures were used, which resulted in improved reaction times.

Example 8

110° C., ee of the L-propane-1,2-diol obtained: 93%.

Example 9

120° C., ee of the L-propane-1,2-diol obtained: 80%.

Example 10

140° C., ee of the L-propane-1,2-diol obtained: 71%.

Examples 11 to 13

The procedure was as in Example 1 except that 5 g of Ru powder were used as the catalyst. The catalyst was recovered after each reaction and re-used in the same reaction. After being recycled 5 times, the catalyst was used successively for reactions at 100° C. and 200 bar in the presence of different solvents.

Example 11

700 g of a mixture of 80% by weight of tetrahydrofuran and 20% by weight of water; ee of the L-propane-1,2-diol obtained: 96%.

Example 12

700 g of a mixture of 80% by weight of methanol and 20% by weight of water; ee of the L-propane-1,2-diol obtained: 94%.

Example 13

700 g of a mixture of 80% by weight of i-propanol and 20% by weight of water; ee of the L-propane-1,2-diol obtained: 95%.

Example 14

150 g of L-tartaric add, 700 ml of water and 20 g of Ru Mohr's salt were placed in a 1.3 l stainless steel autoclave and stirred at a hydrogen pressure of 200 bar and 80° C. until the uptake of hydrogen had ended. After cooling of the reaction mixture, removal of the catalyst by filtration and removal of the water by distillation, 123 g of a clear oil were obtained which crystallized overnight at 4° C. The resulting crystalline mass was recrystallized twice from absolute ethanol to give 86 g of L-butane-1,2,3,4-tetraol in the form of a pure-white solid (m.p. 87°–88° C.; $[\alpha]_D^{20}$+11.6°; c=2, EtOH).

Example 15

135 g of L-malic acid, 700 ml of water and 30 g of Ru Mohr's salt were placed in a 1.3 l stainless steel autoclave and stirred at a hydrogen pressure of 200 bar and 80° C. until the uptake of hydrogen had ended. After cooling, separation of the catalyst by filtration and separation of the water by distillation, 106 g of a clear oil were obtained which was distilled at 1 mbar to give 89 g of 97% pure L-butane-1,2, 4-triol (b.p. 172° C.; $[\alpha]_D^{20}$−26.6°c=1, MeOH).

Example 16

20 g of Ru Mohr's salt and 109 g of S-(−)-2-chloropropionic acid were placed in 700 ml of water in a 3 l stainless steel autoclave. After flushing with nitrogen, the apparatus was dosed and brought to a hydrogen pressure of 100 bar. Over 2 hours the temperature was raised to 140° C. and the hydrogen pressure to 200 bar. The mixture was stirred at 140° C. and 200 bar until the uptake of hydrogen had ended, it was then cooled to room temperature, the catalyst was filtered off and the water was distilled off. The residue obtained was distilled under nitrogen at normal pressure to give 72 g of S-(+)-2-chloropropanol (b.p. 160° C.; $[\alpha]_D^{20}$+14.4° as the liquid) with an ee of 82.3%.

Comparative Example

The procedure was as in Example 1 except that the catalyst used was copper chromite (a conventional hydrogenation catalyst for the reduction of carboxylic acids to alcohols). Up to 150° C., no reaction took place; above 160° C., propane-1,2-diol was accompanied by other reaction products and the propane-1,2-diol was extensively racemized.

Raney nickel (a conventional catalyst for the reduction of carboxylic acid esters to alcohols) was used as the catalyst in another reaction. The nickel partially dissolved during the reaction and no propane-1,2-diol could be isolated from the reaction mixture.

What is claimed is:

1. A process for the preparation of optically active alcohols, in which optically active carboxylic acids are reduced with hydrogen at temperatures below 160° C. and pressures below 250 bar, in the presence of ruthenium catalysts.

2. The process of claim 1, in which the optically active carboxylic acids used are those of the formula (I):

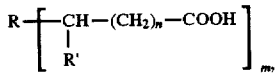

in which m is 1, 2 or 3, n is zero or an integer from 1 to 5 and $R^1$ is a monovalent radical selected from the group consisting of linear and branched $C_1$–$C_{12}$-alkyl, $C_7$–$C_{12}$-aralkyl, $C_6$–$C_{10}$-aryl and $C_1$–$C_{12}$-alkoxy radicals or is hydroxyl or halogen, and if m=1

R is a monovalent radical selected from the group consisting of linear and branched $C_1$–$C_{12}$-alkyl, $C_7$–$C_{12}$-aralkyl, $C_6$–$C_{10}$-aryl and $C_1$–$C_{12}$-alkoxy radicals or is a halogen or hydroxyl radical which is different from R', if m=2

R is absent or is a divalent radical selected from the group consisting of linear and branched $C_1$–$C_{12}$-alkyl, $C_7$–$C_{12}$-aralkyl radicals, if m=3

R is a trivalent radical selected from the group consisting of linear and branched $C_1$–$C_{12}$-alkyl, $C_7$–$C_{12}$-aralkyl radicals, giving optically active alcohols of the formula (II):

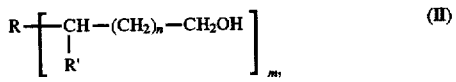

in which m, n, R' and R are as defined for the formula (I).

3. The process of claim 1, in which the optically active carboxylic acids used are those of the formula (I):

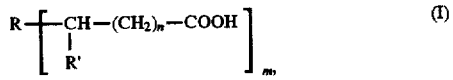

in which m is 1 or 2, n is zero, 1 or 2 and

R' is linear or branched $C_1$–$C_4$-alkyl, benzyl or a hydroxyl, fluorine, chlorine or bromine, and R is different from R' and is linear or branched $C_1$–$C_4$-alkyl, benzyl, hydroxyl, fluorine or chlorine giving optically active alcohols of the formula (II):

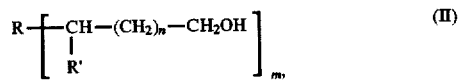

in which m, n, R' and R are as defined.

4. The process of claim 2, in which one of the radicals R' and R is hydroxyl.

5. The process of claim 2, in which if R' and R are alkyl, aralkyl, aryl and/or alkoxy radicals, they are substituted by halogen, hydroxyl, $C_1$–$C_4$-alkoxy, thiol, amino and/or $C_1$–$C_4$-alkylamino radicals and/or contain heteroatoms in the alkyl chain and/or in the aryl moiety.

6. The process of claim 1, in which the optically active carboxylic acid used is optically active lactic acid, optically active tartaric acid, optically active 2-chloropropionic acid or optically active malic acid, giving optically active propane-1,2-diol, optically active 1,2,3,4-tetrahydroxybutane, optically active 2-chloropropanol or optically active 1,2,4-trihydroxybutane respectively.

7. The process of claim 1, in which the ruthenium catalyst used is elemental ruthenium or a ruthenium compound as such.

8. The process of claim 1, in which the ruthenium catalyst used is elemental ruthenium or a ruthenium compound applied to a support.

9. The process of claim 1, in which based on 1 mol of optically active carboxylic acid, 0.1 to 10 g of elemental ruthenium or ruthenium compounds are used.

10. The process of claim 1, in which based on 1 mol of optically active carboxylic acid, 1 to 50 g of ruthenium-containing supported catalyst are used.

11. The process of claim 1, which is carried out in the presence of water, water-miscible solvents or mixtures of the two.

12. The process of claim 1, which is carried out at temperatures in the range 50° to 150° C. and at pressures in the range 5 to 250 bar.

13. The process of claim 1, in which the reaction mixture is worked up firstly by cooling and separation of the catalyst, separation of the readily volatile constituents present by distillation and fractionation of the residue under vacuum.

14. The process of claim 1, in which the reaction mixture is worked up firstly by cooling and separation of the catalyst, separation of the readily volatile constituents present by distillation under slightly reduced pressure and fractionation of the residue under vacuum.

* * * * *